United States Patent

Eisenbraun et al.

Patent Number: 5,118,839
Date of Patent: Jun. 2, 1992

[54] NITRO-SUBSTITUTED POLYARYLKETONES

[75] Inventors: Allan A. Eisenbraun; Venkataraman Ramachandran, both of Baton Rouge, La.

[73] Assignee: Ethyl Corporation, Richmond, Va.

[21] Appl. No.: 576,850

[22] Filed: Sep. 4, 1990

[51] Int. Cl.$^5$ .................. C07C 205/38; C07C 223/06; C07C 49/76; C07C 45/61; C07F 7/04
[52] U.S. Cl. .................... 562/436; 556/436; 560/36; 562/430; 562/432; 562/441; 564/328; 568/25; 568/306; 568/316; 568/323
[58] Field of Search ................. 568/306, 316, 323, 25; 562/420, 436, 430, 432, 441, 488; 556/436; 564/328

[56] References Cited

U.S. PATENT DOCUMENTS 4,413,144 11/1983 Tappe et al. .................. 568/306
4,918,236 4/1990 Knudsen et al. .................. 568/306

FOREIGN PATENT DOCUMENTS 0157740 10/1985 European Pat. Off. .
0212823 3/1987 European Pat. Off. .
1042452 2/1980 Japan .

Primary Examiner—Jose G. Dees
Assistant Examiner—Vera C. Clarke
Attorney, Agent, or Firm—Richard J. Hammond

[57] ABSTRACT

A process for preparing nitro substituted polyarylketones of the formula:

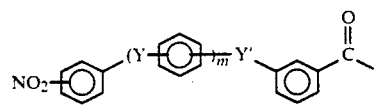

-continued

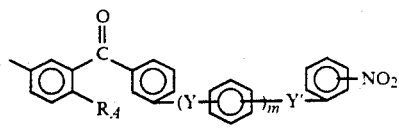

is disclosed. The process involves the condensation of

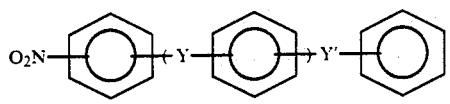

with

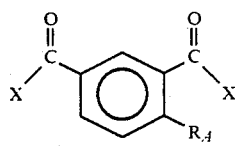

where $R_4$ is hydrogen, —COOH, or $C^1$ to $C_{12}$ linear or branched alkyl, Y and Y' are the same or different and are a chemical bond

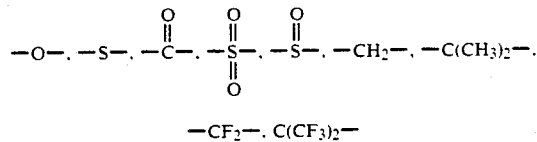

or —Si(CH$_3$)$_2$— and m is 0 or 1 and X is halo.

These nitro groups of these compounds can be reduced to provide the corresponding amines, which are useful for the preparation of thermally stable high melting polyimides.

9 Claims, No Drawings

NITRO-SUBSTITUTED POLYARYLKETONES

The present invention relates to aromatic ketones and methods for preparing such ketones. More particularly, this invention relates to substituted benzophenones, and the dicarboxylic acid, acid esters and acid anhydrides thereof as well as methods of their preparation.

Linear aromatic or heterocyclic condensation-type polyimides have been an item of commerce for over two decades. The polymer systems that have shown the most success are those that utilize the reaction product of an aromatic dianhydride and aromatic diamine. Because of the difficulty in shaping or other processing of the polyimides produced from the above starting materials, it has been found more convenient to first form a solution of polyamic acid intermediate, and then to thermally or chemically imidize this intermediate. It has further been found that the control of the physical properties of the final polymer by use of certain selected starting materials can dramatically affect the processing of the polymer. Thus starting materials of high molecular flexibility provide polymers having good final physical properties but at the same time are readily processable. Diamines with flexibilizing groups (—O— —S— etc.) have been effectively employed in producing polyimides that are easy to process. These materials are difficult to prepare and their use has therefore been limited.

It would be advantageous to have an improved process for producing aromatic diamines having flexibilizing groups in the molecule.

A new process has been discovered to prepare compositions of matter that can be used as chain extending agents for the preparation of more easily processable polyimides. These compositions are substituted benzophenones and the dicarboxylic acids, acid esters and anhydrides thereof.

Aromatic ketones of use in the process of the present invention are those unsymmetric compounds having the formula $$R_A \text{-Ar-C(O)-Ar-(Y-Ar)}_m\text{-Y'-Ar-R} \quad \text{I}$$

where R is nitro or amino, $R_A$ is the same or different than $R_B$ and individually are hydrogen, —COOH, —COOR$_1$ or taken together form an anhydride ring where $R_1$ is $C_1$ to $C_{12}$ linear or branched alkyl with the proviso that both $R_A$ and $R_B$ can not be hydrogen, Y and Y' are the same or different and are a chemical bond, $$-O-, -S-, -\overset{O}{\underset{\|}{C}}-, -\overset{O}{\underset{\underset{O}{\|}}{\underset{\|}{S}}}-, -S-, -CH_2-, -C(CH_3)_2-,$$

$$-CF_2-, C(CF_3)_2-$$

or —Si(CH$_3$)$_2$—, and m is 0 or 1, e.g., when $R_A$ and $R_B$ are taken together and form an anhydride ring are the compounds $$\text{(anhydride)-Ar-C(O)-Ar-(Y-Ar)}_m\text{-Y'-Ar-R} \quad \text{II}$$

In the above compounds of formula II, the group R is nitro or amino and Y, Y' and m are as defined above.

In the compounds of formula I, it is preferred that $R_A$ and $R_B$ are the same and are the group carboxylic acid (i.e. —COOH), or esters thereof or the anhydrides illustrated by the compounds of formula II. Thus, those preferred compounds of formula I can be the free dicarboxylic acids i.e., $R_A = R_B = $ —COOH or their esters, i.e., $R_A$ and $R_B$ are —COOR$_1$ where $R_1$ is $C_1$ to $C_6$ linear or branched alkyl. Typical esters are the methyl, ethyl, n-propyl, n-butyl, n-pentyl, and n-hexyl esters.

In the above preferred compounds preferably m is 0 and Y' is a chemical bond, —O—, —CH$_2$—, $$-\overset{O}{\underset{\|}{C}}-,$$

—C(CH$_3$)$_2$—, or —C(CF$_3$)$_2$.

In the compounds useful in the process of the present invention R is preferably amino.

The most preferable of the compounds of the present invention are those of formula I where $R_A$ and $R_B$ are taken together to form the anhydride ring, m is 0 and Y' is —O—.

The compounds of the process of the present invention where R is amino are prepared by the facile reduction of the corresponding nitro precursors (to the free amine group). A variety of reducing agents can be used to carry out such reduction, i.e., hydrogen with Pd on carbon catalyst, lithium aluminum hydride, Raney nickel, etc.

Illustrative of the compounds of the present invention are the following:

benzophenone-4-(4″-nitrophenyl)-3′,4′-dicarboxylic acid;
benzophenone-4-(4″-nitrophenyl)-3′,4′-dicarboxylic acid dimethyl ester;
benzophenone-4-(4″-nitrophenyl)-3′,4′-dicarboxylic acid diethyl ester;
benzophenone-4-(4″-aminophenyl)-3′,4′-dicarboxylic acid;
benzophenone-4-(4″(aminophenyl)-3′,4′-dicarboxylic acid dimethyl ester;
benzophenone-4-(4″(aminophenyl)-3′,4′-dicarboxylic acid diethyl ester;
benzophenone-aminophenyl-3,′4,′-dicarboxylic acid anhydride;
benzophenone-2-(4″-nitrophenyl)-3′,4′-dicarboxylic acid;
benzophenone-2-(4″-nitrophenyl)-3′,4′-dicarboxylic acid dimethyl ester;
benzophenone-2-(4″-nitrophenyl)-3′,4′-dicarboxylic acid diethyl ester;
benzophenone-2-(4″-aminophenyl)-3′,4′-dicarboxylic acid;
benzophenone-2-(4″(aminophenyl)-3′,4′-dicarboxylic acid dimethyl ester;
benzophenone-2-(4″(aminophenyl)-3′,4′-dicarboxylic acid diethyl ester;

benzophenone-N-phenylaminophenyl-3,'4,'-dicarboxylic acid anhydride;

As noted earlier the compounds used in the process of the present invention are readily prepared by the well known Friedel Crafts acylation procedure, i.e.,

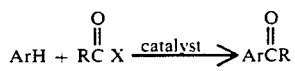

where Ar is an aromatic nucleus, X is halo (chloro, bromo or iodo) and R is aryl or alkyl such as the group

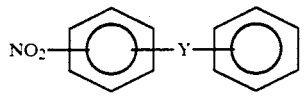

where Y is as previously defined.

In such reaction, catalysts are typically of the Lewis or Bronsted acid type, such illustrated by ferric chloride, aluminum chloride, boron trifluoride, etc. However, in the preferred embodiment of the present invention triflic acid (trifluoromethanesulfonic acid, $CF_3SO_3H$) or similar sulfonic acids have proven to be especially active acylation catalysts. Thus acids known in the art as Super acids such including fluorosulfonic acid, Magic Acid (hydrofluoric acid and antimony pentafluoride) as well as other halo fluoromethanesulfonic acids are useful in causing the reaction to prepare the compounds of the present invention. The following reaction path is illustrative of the preferred method of preparation of the compounds

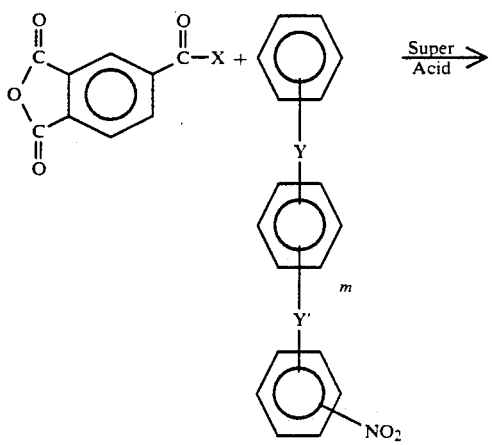

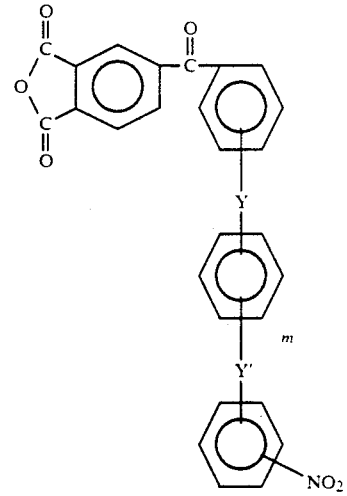

Because these superacids are exceptionally active in causing the acylation to occur as shown above, the general requirement of having a 1:1 mole ratio of acyl halide to Lewis Acid does not apply. See for example U.S. Pat. No. 4,802,791. Thus, surprisingly small amounts of super acid are effective in causing the acylation reaction. From about 0.1% by weight to about 50% by weight of super acid based on the amount of acyl halide will catalyze this reaction. Depending on the reactivity of the aromatic hydrocarbon, i.e., methyl substituted are more reactive than unsubstituted ones; smaller amounts of triflic acid can be used (<0.1% preferred).

It should be noted that difunctional aromatic acyl halides of the formula

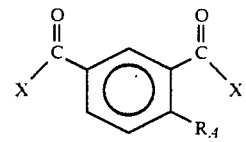

where X, Y and $R_A$ are as previously defined can be controllably reacted with the same or a similar nitroaromatic compound to form compounds of the formula

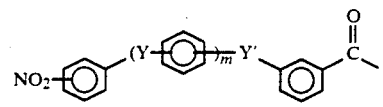

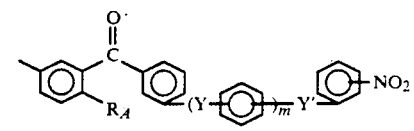

where m and Y' are as previously defined, using the same conditions employed for the mono acyl halide. Mole reaction ratios must be adjusted to accommodate this reaction sequence, i.e. two moles of nitro starting material to one of acid halide. Reduction of the above dinitro compounds will, of course, produce the diamino derivative. Compounds of this type are useful in the preparation of polyimides or polyamides by reaction with dianhydrides or diacids (or diacid chlorides) as is well known. See for example the relevant chapter in Encyclopedia of Polymer Science Technology, Mark et al editors, Interscience Publishers, incorporated herein by reference.

As discussed earlier, concerning the amount of $CF_3SO_3H$ necessary to affect the conversion, activated aromatics require lower temperatures than do the deactivated ones. Thus, from about 0.1% by weight to about 25% by weight of super acid based on the amount of acyl halide is preferred to catalyze the reaction.

As indicated from the reaction path shown above, the initial reaction to form the compounds used in the process of the present invention is a modification of the Friedel Crafts acylation reaction utilizing an anhydride-substituted aromatic acid halide. The product of the reaction is anhydridesubstituted benzophenone compound of formula II. These compounds can be readily transformed into the compounds of formula I where $R_A$ and $R_B$ are the same or different and are $C_1$ to $C_{12}$ linear or branched alkyl esters by an alcoholysis reaction, i.e., reaction of the anhydride with an aliphatic alcohol. While the reaction is typically catalyzed by acids e.g., $H_2SO_4$, Lewis Acids or bases, the preferred catalyst is pyridine or a dilute alcoholic solution of an alkali metal hydroxide.

Similarly, rather than alcoholysis, the compounds of formula I can be converted to the dicarboxylic acids (where $R_A$ and $R_B$ are both the group —COOH) by simple hydrolysis, e.g., reaction with water. Such reaction may be conducted with or without a catalyst, e.g., an organic or inorganic base.

The alcoholysis reaction and the hydrolysis reaction of the anhydride of the compounds of formula I are well known in the prior art. See for example, the text by March, Advanced Organic Chemistry, McGraw-Hill, New York, N.Y., referred to earlier.

Oxidation of compounds of Formula 1 where $R_A$ and $R_B$ are alkyl ester carboxylate groups will to lead to benzophenonetetracarboxylic acids, monomers that are useful in polyimide preparations.

In order for those skilled in the art to be better able to practice the present invention, the following are given by way of illustration and are not to be taken as limiting the scope of the invention in any way.

EXAMPLE 1

Synthesis of
1,3-bis[4-nitrophenoxy)-4'-benzoyl]benzene (BNBB):

A mixture of 4-nitrophenyl phenyl ether (5.0 g), isophthaloyl dichloride (2.4 g) and triflic acid (0.02 g) was stirred under nitrogen for 5.5 hours at 198° C. The reaction mixture was taken up in toluene (100 ml) and stirred with 10% caustic for 30 minutes. The pH of the solution was brought to 7 and the organic layer was separated, dried with anhydrous $Na_2SO_4$ and the toluene stripped off. The residue was crystallized from isopropanol, and dried to give 1.8 g of product. NMR and Mass Spectral data were consistent with the structure. Additional 1.2 g of BNBB was recovered from the mother liquor. Total amount of product recovered was 3 g accounting for a 45% overall yield based on the initial amount of isophthaloyl chloride.

EXAMPLE 2

Synthesis of
1,3-bis[4-aminophenoxy)-4'-benzoyl]benzene (BABB):

A 1 g sample of BNBB in 25 ml ethyl acetate was catalytically hydrogenated at room temperature. An initial pressure of 60 psi was maintained for three hours and the reaction continued further overnight. In the end the reaction mixture was filtered and the excess solvent was removed to give a foamy product (0.93 g). The spectral data was consistent with the structure of BABB.

EXAMPLE 3

Preparation of
benzophenone-3,4-dimethyl-3',4'-dicarboxylic acid:

Stirred a mixture of trimellitic anhydride chloride (10.5 g), o-xylene (22.5 g) and triflic acid (130 mg) at 150° C. bath temperature under $N_2$ for 3 hours, after which the reaction mixture was cooled to room temperature and 25 ml o-xylene and 50 ml of water was added. Under constant stirring a 50% aqueous NaOH solution was slowly added to the reaction mixture until pH was around 12-13. After stopping the agitation the phases were allowed to separate and the organic phase was discarded. The basic aqueous phase was slowly neutralized with con. $H_2SO_4$ until pH 2 and the solid formed was filtered, washed with water and dried in vacuum oven at about 80° C., to give 9.52 g of yellow solid, the GC analysis of which showed two major products in 86:14 ratio. A 1 g sample of this product was digested in a hot dilute 1-propyl alcohol solution (50 ml $H_2O$/5 ml IPA) until all the solids dissolved. The solution was then cooled to room temperature and the solid formed was filtered, washed with water and dried at 60°-80° C. for 4 hours in a vacuum oven. 460 mg of shinny pale yellow solid (97% by GC area % analysis) was obtained, whose structure was determined by a combination of GC/MS (exact mass determination of bis-trimethylsilyl derivative of the solid) and $^1H$ and $^{13}C$ NMR spectra. The exact mass is determined as 442.1627 corresponding to $C_{23}H_{30}Si_2O_5$. $^1H$ NMR (d$_6$-DMSO):2.274 (s, 3H, $CH_3$), 2.299 (s, 3H, $CH_3$), 7.30-7.33 (d, 1H, Ar-H), 7.44-7.47 (doublet of doublet, J=1.4 Hz, J=7.8 Hz, 1H, Ar-H), 7.538 (d, J=1.4 Hz, 1H, Ar-H), 7.763-7.789 (d, J=7.9 Hz, 1H, Ar-H), 7.845-7.877 (doublet of doublet, J=1.7 Hz, J=8.0 Hz, Ar-H), 7.943-7.948 (d, J=1.7 Hz, 1H, Ar-H). The major product of the above reaction was thus determined to be benzophenone-3,4-dimethyl-3',4'-dicarboxylic acid and the total isolated amount of it is 8.2 g (55% yield based on trimellitic anhydride chloride used initially).

We claim:

1. A process for producing a compound of the formula

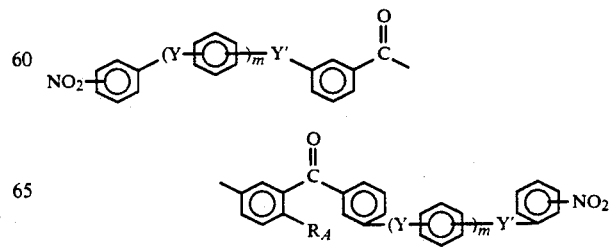

where $R_A$ is hydrogen, COOH or $C_1$ to $C_{12}$ linear or branched alkyl, Y and Y' are the same or different and are a chemical bond,

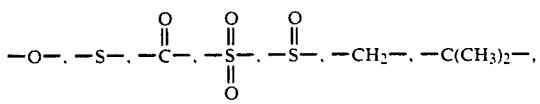

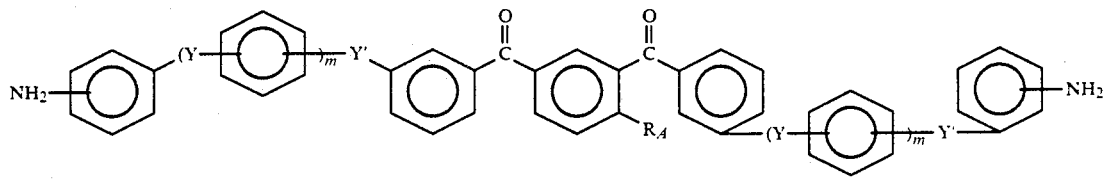

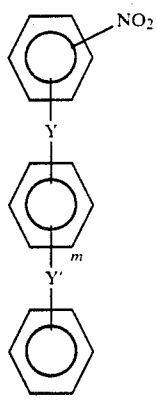

with an aromatic di acid halide of the formula

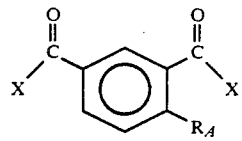

where X is halo and Y, Y' and $R_A$ are as previously defined.

2. The process according to claim 1 wherein the catalyst in said catalytic treating is triflic acid.

3. The process according to claim 1 wherein $R_A$ is —COOH.

4. The process according to claim 3 wherein m is 0 and Y is a chemical bond,

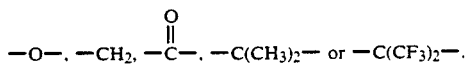

5. The process according to claim 4 wherein Y is —O—.

6. The process according to claim 5 wherein the catalyst in said catalytic treating is trifluoromethanesulfonic acid.

7. A process for producing a compound of the formula

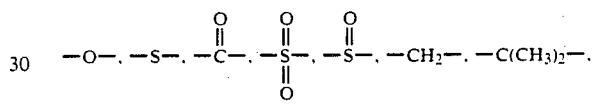

where $R_A$ is hydrogen, COOH or $C_1$ to $C_{12}$ linear or branched alkyl, Y and Y' are the same or different and are a chemical bond, $$-O-, -S-, -\overset{O}{\underset{}{\overset{\|}{C}}}-, -\overset{O}{\underset{O}{\overset{\|}{\underset{\|}{S}}}}-, -\overset{O}{\underset{}{\overset{\|}{S}}}-, -CH_2-, -C(CH_3)_2-,$$

$-CF_2-, C(CF_3)_2-$ or $-Si(CH_3)_2-$ and m is 0 or 1.
comprising catalytically treating with a super acid a nitroaromatic compound of the formula

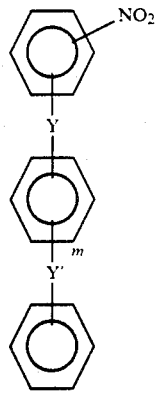

with an aromatic di acid halide of the formula

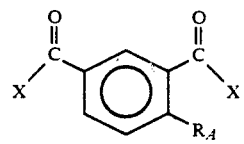

where X is halo and m, Y, Y' and $R_A$ are as previously defined and reducing the compound formed from said super acid treatment.

8. A process for producing a compound of the formula

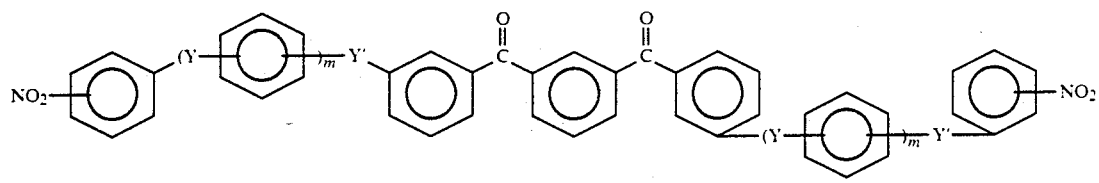
where Y and Y' are the same or different and are a chemical bond,
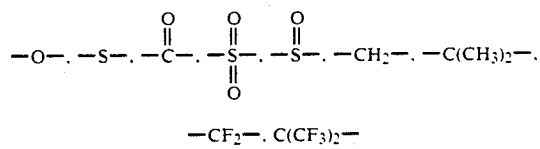
or —Si(CH$_3$)$_2$— and m is 0 or 1
comprising catalytically treating with a super acid a nitroaromatic compound of the formula
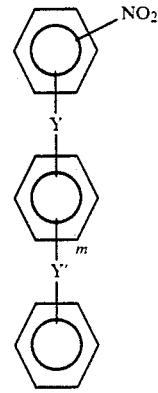
with an aromatic di acid halide of the formula
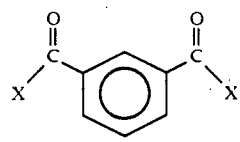
where X is halo and Y and Y' are as previously defined.
9. The process according to claim 8 where m is 0 and Y is a chemical bond.
* * * * *